United States Patent
Du et al.

(10) Patent No.: US 10,219,713 B2
(45) Date of Patent: Mar. 5, 2019

(54) COMPACT WEARABLE PHONOCARDIOGRAM AND ELECTROCARDIOGRAM CONTINUOUS MONITORING SYSTEM

(71) Applicant: Bayland Scientific LLC, Fremont, CA (US)

(72) Inventors: Xiaosong Du, San Ramon, CA (US); Yuxin Zhou, Fremont, CA (US)

(73) Assignee: BAYLAND SCIENTIFIC LLC, Fremont, CA (US)

( * ) Notice: Subject to any disclaimer, the term of this patent is extended or adjusted under 35 U.S.C. 154(b) by 0 days.

(21) Appl. No.: 15/156,098

(22) Filed: May 16, 2016

(65) Prior Publication Data

US 2018/0168473 A1 Jun. 21, 2018

Related U.S. Application Data

(60) Provisional application No. 62/161,890, filed on May 15, 2015.

(51) Int. Cl.
  *A61B 7/04* (2006.01)
  *A61B 5/00* (2006.01)
  *A61B 5/0408* (2006.01)

(52) U.S. Cl.
  CPC ........ *A61B 5/04085* (2013.01); *A61B 5/0022* (2013.01); *A61B 5/6833* (2013.01); *A61B 5/7214* (2013.01); *A61B 7/04* (2013.01); *A61B 2560/0204* (2013.01)

(58) Field of Classification Search
  CPC .... A61B 5/0402; A61B 5/0006; A61B 5/0022
  USPC ........................................................ 600/513
  See application file for complete search history.

(56) References Cited

U.S. PATENT DOCUMENTS

2012/0330126 A1* 12/2012 Hoppe ................. A61B 5/0002
                                                                600/391
2016/0328530 A1* 11/2016 Felemban ............... H04W 4/70

* cited by examiner

*Primary Examiner* — Amanda K Hulbert
*Assistant Examiner* — Philip C Edwards
(74) *Attorney, Agent, or Firm* — Helen Mao; Imperium Patent Works (57) ABSTRACT

Apparatus and method are provided to collect and analyze phonocardiogram (PCG) an electrocardiogram (ECG) waveforms. In one novel aspect, the PCG and ECG waveforms are collected from wearable devices. In one embodiment, the wearable device collects heartbeat waveforms by attaching the device to the patient for a long period and sends the collected waveforms to a receiver through a wireless network. In one embodiment, an acoustic seal layer is attached to the wearable device to reduce the body movement noises and environmental noises. In another novel aspect, an analysis method compares received patient's current PCG/ECG waveform with historic data. In one embodiment, the historic data are stored in a cloud-based database.

7 Claims, 7 Drawing Sheets

COMPACT WEARABLE PHONOCARDIOGRAM AND ELECTROCARDIOGRAM CONTINUOUS MONITORING SYSTEM

CROSS REFERENCE TO RELATED APPLICATIONS

This application claims priority under 35 U.S.C. § 119 from U.S. Provisional Application Number 62/161,890 entitled "METHOD AND APPARATUS OF COMPACT WEARABLE PHONOCARDIOGRAM AND ELECTROCARDIOGRAM CONTINUOUS MONITORING SYSTEM," filed on May 15, 2015, the subject matter of which is incorporated herein by reference.

TECHNICAL FIELD

The present invention relates generally to mobile heartbeat and breathing waveform continuous monitoring and, more particularly, devices and system for the compact wearable phonocardiogram and electrocardiogram continuous monitoring system.

BACKGROUND

For the past decade, there are significant progresses in medical research. The Human Genome Project had finished. For the first time in history, we have decoded over 20,000 human genes. The stem cell researchers have already safely injected stem cells into patients with neurodegenerative diseases and spinal cord injuries and they have seen the potential to vastly improve lives. MRI and other medical imaging technologies continuously improved, more and more advanced electronic devices, sensors, networking, data mining technologies are used in hospitals. Despite these great achievements, most of us still rely on once or twice annual doctor visits to get our physicals. None of these great technologies is used to monitor our day-to-day health status, not mention more sophisticated day-to-day health analysis and disease detection. Many people jokes that they know their cars better than their bodies. In many ways, it is a true statement. There are over 100 sensors on a modern car. On the other hand, the sensor to monitor our vital life is close to zero.

Today, one out of four deaths in the United States is due to cardiac disease, and two out of five disease caused death in China is due to cardiovascular disease. Only 1% of new born have heart defects, combining these two facts, there is a very serious heart health degradation progressing in average people's life span. Most of annual physical checkup do not provide comprehensive heart exam unless doctors hear the complain of chest pain, short breathe . . . at this point, the degradation already progressed enough to make patient feel uncomfortable. Like all the life threatening disease, early detection is the key, because people can not only adjust habit to get long term benefit for heart, but keep themselves away from some stressful activities once some symptom showed up from the detection. Although medical researcher had warned that many chronicle diseases, like diabetes and unhealthy life styles, such as smoking, obesity can eventually cause heart problems, due to lack of effective long term monitoring device and analysis tool, how the heart disease gradually developed is still a mystery. There is a tremendous value to provide a household based device that can monitor and record the heart status and performance and also be able to understand the measurement not only in absolute numbers but also in past statistic and also to similar population. The information can motivate people to live in healthier life style and improve life quality.

The conventional stethoscope has proven to be useful tools for doctor in the past two hundred years. However, they are targeted to bulky, clinic oriented environment. To early detect cardiac abnormality development, it is beneficial to have a compact, ruggedized, self-explainable device and system solution be available in household to help general public understand the heart mechanical activity and electrical activity in their daily activities.

The electrocardiogram reflects the triggering signal of heart pumping. After the electrocardiogram peak, the heart pumps the blood into the heart; then drives them out. During this process, two distinct sounds are generated. When we monitor the electrocardiogram and phonocardiograph simultaneously, we can observe that the electrocardiogram will have a peak ahead of the two peaks in phonocardiograph. Although the time difference is very small for healthy people, it is very time critical for patients with heart diseases. Most of the heart failure and other forms of cardiovascular diseases are developed during a long span of time. It may easily take a decade to develop. At the early stage, there is no obvious discomfort on the patient side, and it is very hard to catch the abnormal heart behavior during a short period such as during the patient annual checkup. However, when the patient does feel the discomfort, it is usually too late. To effective prevent this kind of disease; it is extremely valuable to have a small, easy to carry and easy to use wearable device that can simultaneously monitor both electrocardiogram and phonocardiograph continuously. The data are automatically archived and compared against various disease patterns, or with the user's previous data. The abnormal trend of change can be observed and be prompted to the user or medical professionals to prevent the further development of the disease.

Although it is necessary to have a small and easy to use wearable device to patch on the heart of the user and simultaneously monitor the electrocardiogram and phonocardiograph, there are many challenges to develop this kind of device and related software. For the past two hundred years, to collect phonocardiogram, a heavy and bulky stethoscope head is employed. Meanwhile, the electrocardiogram device is also very bulky and cumbersome. It requires a set of wire and patches are attached to various part of the chest of the user. It makes impossible for a general user without advance medical knowledge or training to use them on a daily basis.

Further challenge comes that all the prior arts require the medical professionals to interpolate the results. However, when this device becomes a general household health monitoring equipment, millions of people may use it on a daily basis. It immediately becomes impractical to rely on medical professionals to scan through the sampled data and interpolate them. It is necessary to have a backend analysis software to automatically analyze and screen the data; identify the abnormal pattern or trend and feedback to user or medical professionals for further monitoring or examination.

SUMMARY

Apparatus and method are provided to monitor heartbeat waveform and breathing waveform continuously on daily basis.

In one novel aspect, a wearable waveform-collecting device can be attached to a human body to collect PCG and ECG waveforms continuously on daily basis. The wearable waveform-collecting device transmits the collected information to a smart device over a wireless network.

In one embodiment, a wearable patch includes compact digital sensors. It includes a device with function of acquiring heart sounds and measure the cardiac electrical signal; transmitting these signal to a mobile or PC wirelessly or through wire connection; the field data can be upload to a remote server, wherein it performs the data processing and analyzing; the result can be downloaded to field mobile device or PC to provide on-time feedback; it also includes a patching mechanism to allow the device in use without interfering general daily activities. The measured phonocardiogram (PCG) and electrocardiogram (ECG) waveform is transferred to remote processor in real time or off-line by wireless link or readout I/O devices. The continuous monitoring these waveforms for a long time span, more than several hours, to disclose early abnormalities. This continuous monitored waveform can be characterized and compared with the user's previous measurements and various known disease waveforms and characteristics through smart phones, smart watch, computers, and other browsing devices. The health alarms or recommendations to the user can be drawn from the characterizations. The user can use them as reference and pursue further medical help. The waveforms and characteristics are automatically archived. With the user's data can be used by medical professionals or other institutes for further analysis or reference. The medical researchers, data processing, and data mining expertise can utilize the large amount of waveforms and characterizations to do in depth research and exploration. Their research can lead to more advanced method for waveform analysis and characterization, which can apply to the general users. The users can choose what kind of advanced analysis they want to apply. Certain charges can be associated with the advanced analysis so that the researchers and expertise can be awarded by their discoveries.

In one embodiment, the PCG and ECG waveforms are synced together over a period on one chart to have a more comprehensive understanding of the heart activity. In another embodiment, a series of acoustic sensors are designed to receive sound differently from different direction to enhance to noise immunity. In yet another embodiment, several sound sensors and ECG probes can be employed to have the capability of measuring several test points on the chest simultaneously. In the scenario of using a series of acoustic sensors, multiple miniature stethoscope heads can be employed to hear from chest and back at the same time.

In yet another aspect of the present invention, a silicone sheet can be performed to patch the waveform collecting and transmission module on the chest without any additional attention. In yet another embodiment of the present invention, a smart phone, tablet, or other smart device is used to set up, control, and charge the waveform collecting and transmission module. It is also used to collect the waveform data through wireless network; then transmit the waveform data to remote data centers through wireless network for further analysis and archive. The user can use the screen of the smart device to view various waveforms to make sure the waveform collecting and transmission module is mounted correctly. The user can use the screen to view the analysis and characterization results, get alarms and advices from the remote data center. The battery status is also displayed on the mobile device.

In another novel aspect, a laptop, PC, or dedicated local server can be used to collect the waveform data through the wireless communication with the device. It can be used to set up, control, and charge the waveform collecting and transmission module. The collected waveform data can be stored, archived locally, and can be uploaded to remote data centers through wired or wireless network. The user can use the screen of the notebook, the desktop computer or the local server to view the analysis and characterization results, get alarms and advices from the remote data centers. The battery status is also displayed on this computer.

In yet another embodiment of the present invention, data centers are used to organize all the waveform. Various data processing algorithms are applied to the collected waveform to characterize the waveform. The data centers consist of web servers, databases, data processing hardware and software. High speed network is used to connect them together. In yet another embodiment of the present invention, the PCG and ECG waveforms are cross checked to validate the data before further process. The invalid data is stored and marked, while the valid data is further processed by applying data analysis algorithms to extract characterization parameters. The results can be displayed together with user's previous statistics, also in the larger population statistic with various categories. Also compare his or her peer parameters against various known disease parameters. The original waveform, the analysis and characterization results are archived, downloadable, and also can be emailed by user.

In one embodiment of the present invention, this web server also provides a forum for the users to discuss about the data with other interest party about their experience of using the devices and system. In another embodiment of the present invention, the user can manage his or her data privacy through the web site. The user can give permission to his or her partner so that the waveform and analysis and characterization results can be accessed by the authorized party. In yet another embodiment of the present invention, the device can be used associated with other medical devices, such as glucose monitoring device, insulin pump, as a compliment device to monitor the heart status of the user. The data collected by the other medical devices can be combined with the heart monitoring device and send back to the data center for archive and further analysis. The medical professionals, researchers and data mining experts can utilize these data to do in depth analysis.

BRIEF DESCRIPTION OF THE DRAWINGS

The accompanying drawings, where like numerals indicate like components, illustrate embodiments of the invention.

FIG. 1 is a block diagram of an embodiment of the present invention. It illustrates the system and the function of each component.

DETAILED DESCRIPTION

Reference will now be made in detail to some embodiments of the invention, examples of which are illustrated in the accompanying drawings.

Based on technologies achievements and their broad acceptance, it is feasible to develop a set of sensors to monitor our daily vital health status, transfer these data through wired or wireless Internet to the Cloud storage. These data are archived and analyzed against the user's previous data and against various disease patterns. Health advices can be given as the result of the analysis. Furthermore, the archived data can be used by medical professionals to diagnose diseases. Sophisticated data mining can be performed on the vast daily health data from millions of people. It is very likely to lead to new medical discoveries.

The present invention provides a method, an apparatus, a computer program and a system that provides a series of compact digital sensors that is wearable by patching. The measured waveform is transferred to remote processor in real time or off-line by wireless link or readout I/O devices. The continuously monitoring waveform for a long time span, more than several hours, helps to disclose any early abnormalities. The continuously monitored waveform is characterized and compared with a database of large size samples, which include the user's previous waveforms and characterizations and various known disease waveforms and their characterizations. The user can browse the current and historic waveforms and characterizations through smart phones, smart watch, computers, and other browsing devices. The health alarms or recommendations to the user can be drawn from the characterizations. The user can use them as reference and pursue further medical help. The waveforms and characterizations are automatically archived. With the user's permission, these waveforms and characterizations can be released to medical professionals or other institutes for further analysis or reference. The medical researchers, data processing, and data mining expertise can utilize the large amount of waveforms and characterizations to do in depth research and exploration. Their research can lead to more advanced method for waveform analysis and characterization, which can apply to the general users. The users can choose what kind of advanced analysis they want to apply. Certain charges can be associated with the advanced analysis so that the researchers and expertise can be awarded by their discoveries.

Figure 1:
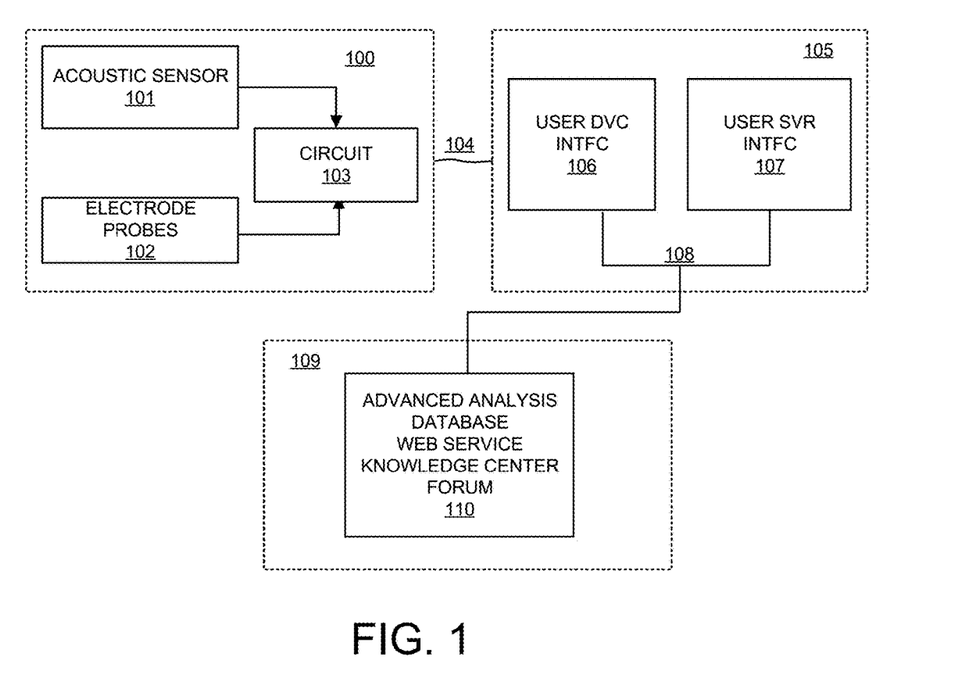
FIG. 1 is a schematic view of a continuous heartbeat and breathing waveform monitoring system in accordance to embodiments of the current invention.

FIG. 1 is a block diagram of a preferred embodiment of the present invention used as a continuous electrocardiogram and phonocardiogram waveform monitor. It consists of a wearable waveform collecting and transmission module (100), a local wireless network (104), smart terminals and local storage (105), the Internet (108), remote data centers (109). The wearable waveform collecting and transmission module (100) also referred as the wearable device, patches on the chest of the user using a preformed silicone gel kind of patch. It uses acoustic-to-electric sensors such as accelerometer, piezo sensor, or microphone behind the shell to detect the acoustic signal. It also uses electrical voltage probe array mounted in the shell to measure the electrical signal on the chest skin. These weak, noisy electrical signals are fed into several different circuits (103) to be filtered, amplified, and some noises are cancelled. The signal is digitized by a processor circuit (103) and the processor circuit communicates to the host PC or tablet or smart phone through the wireless communication protocol such as Bluetooth, low energy Bluetooth, ZigBee, ANT, WiFi, depends on the circuit implementation (103). The digitized waveforms can also be stored into the wearable devices' (100) local storage circuit (103), such as flash memory or EEPROM memory chips (103). The wearable device (100) can communicate with smart device (105), such as smart phone, tablet, smart watch and PC, laptop, through local wireless network (104), such as Bluetooth or Wifi. The smart device, computer can be used to set up and control the module, monitor the waveform in real time, browse the stored waveforms, transfer the stored the waveforms to their local storages, and relay the transmission through wired or wireless networks (108) to remote data centers (109). The local host of smart device, computer can be used to receive the analysis report, alarm, and advices from the remote data centers for user to review. These waveforms are archived and stored in the remote data centers. The waveforms are automatically analyzed and characterized, which includes, but not limited to, comparing with user's historic waveforms, with various known condition patterns, also comparing with data from larger population, also the population can be filtered with conditions defined by user to have some similarity with user to understand user's relative performance among relevant population. The report are automatically generated and sent to the user. The user can also login the website of the remote data centers (109) to view the report and historic data, access the related knowledge and exchange opinion with other users thorough the forum. It can also be used to monitor other body waveforms, for example, monitor sounds from lung, from the baby heartbeat for pregnant women.

Figure 2A:
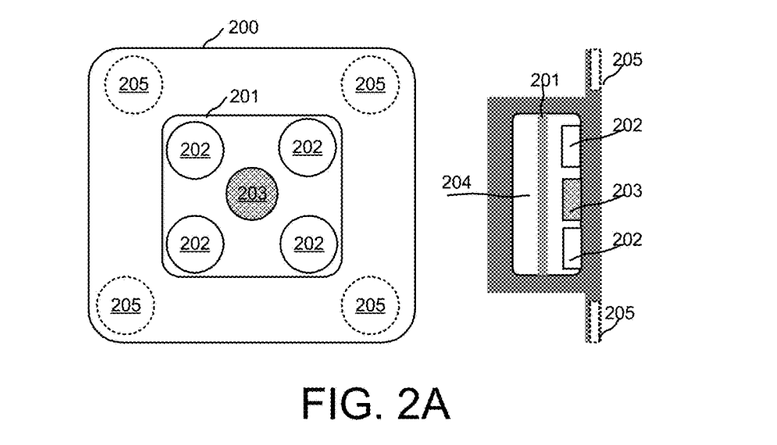
FIG. 2A is a bottom view and cross section of the compact wearable device.

FIG. 2A is the bottom view and cross section view of the wearable device. The device includes preformed patch (200), a circuit and sensors container (201), electrodes (202), and acoustic sensor (203), and circuit assembly (204) which consists of PCB, amplifier circuits, filters, noise suppression circuits, connector, battery charging circuit and battery. In one embodiment, container 201 is a rigid container. Container 201 has an inner chamber and an outer surface. There are four voltage probe electrodes (202) shown in the picture, and the different implementation can have different number of probe electrodes to optimize for each application. Because of the wearable requirement, the physical size of device is small (<35 mm×35 mm), thin (<10 mm) and light <40 g. The patch (200) provides sufficient mechanical support to make the device have good contact to the skin, also provides noise reduction due to the fiction from body movement and environmental noise. In another embodiment, the electrodes are added onto the patch (205), which allows more points to be tested and it can work with a smaller electrode free housing to make the device more portable and offer different electrodes option.

Figure 2B:
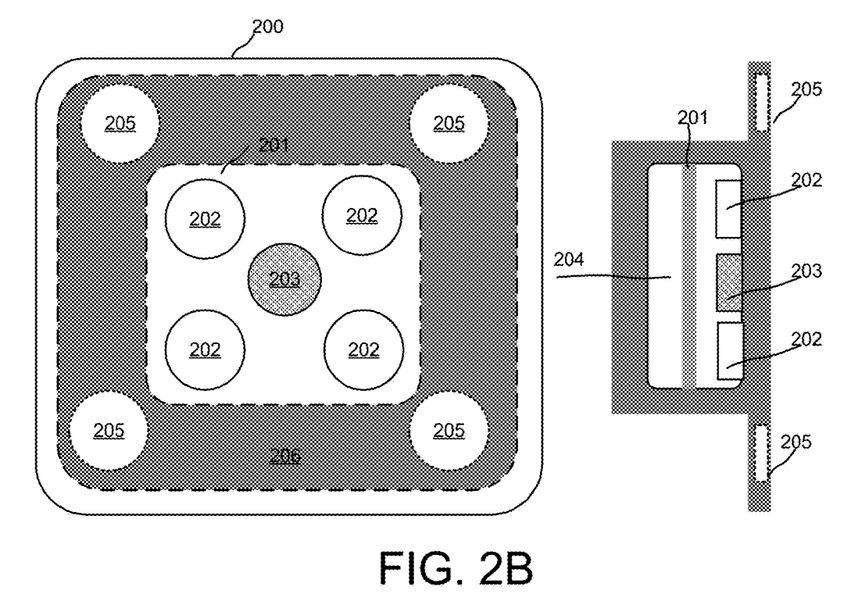
FIG. 2B is bottom view and cross section of the compact wearable device with a ring an acoustic seal.

FIG. 2B is bottom view and cross section of the compact wearable device with a ring an acoustic seal. FIG. 2B shows a similar layout as FIG. 2A. A ring of acoustic seal encloses the sensors is added. The patch (200) with a ring of medical grade adhesive (206) provides sufficient mechanical support to make the device have good contact to the skin, also provides noise reduction due to the fiction from body movement and environmental noise. In another embodiment, the electrodes are added onto the patch (205), which allows more points to be tested and it can work with a smaller electrode free housing to make the device more portable and offer different electrodes option. Inside the patch (200), there is a ring of medical grade adhesive (206) so that the patch can be patched to human body. Meanwhile they seal the micro acoustic chamber and acoustic sensor (203) from the friction noise of body movement and environmental noise.

Figure 3:
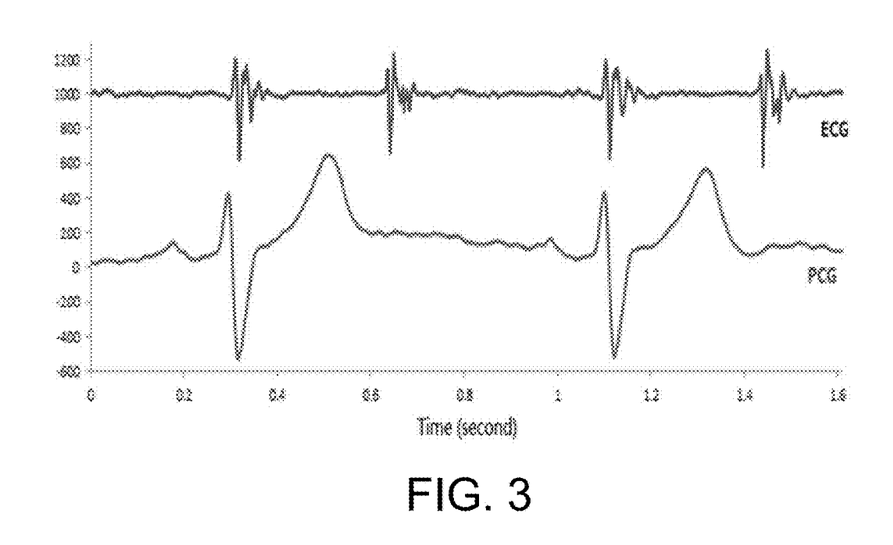
FIG. 3 is the waveform of phonocardiogram and electrocardiogram from the device.

In one embodiment, the wearable device has acoustic sensors with micro acoustic chamber (203) combined with the preformed patch (200) with a ring of medical grade adhesive (206) to replace the traditional heavy and bulky stethoscope head so that the whole sensing device is light weight and can be patched onto the fixed body location for a long time without discomfort. First, it guaranteed the consistence of the signal gathering. Second, it seals the micro acoustic chamber and sensor to prevent environmental noise and friction noise from the body movement. This design greatly enhances the noise immunity of the whole system so that it can detect high quality heart sound in a noisy airplane cabin (about 80 dB), which the prior instruments can never achieve. The traditional stethoscope or digital stethoscope can only be used in very quiet clinic environment. In another aspect, the traditional ECG employs multiple electrodes and uses long wires to link them to a central device to collect test result. It is not a big issue for standard clinic usage. However, it becomes very cumbersome and almost impractical for general consumer to stick multiple electrodes on various body parts and carry these wires around on a daily basis. The presented invention employs multiple electrodes (202) in a concentrated area so that they can work closely with the preformed patch (200) with a ring of medical grade adhesive (206) and micro acoustic chamber and acoustic sensor (203). The optional electrodes (205) can be employed to add more testing points. The whole device with multiple sensors can be patched onto the body and later take off as one piece, just like using a normal Band-Aid. Since the multiple sensors are patched to close to heart, it enables to monitor both ECG (310) and PCG (311) in a synchronized manner.

FIG. 3 Shows ECG (310) and PCG (311) waveform collected by this wearable device. Depends on the combination of the electrodes position, several ECG outputs can be configured through host device's user interface. The local host device collects, displays, and records the measurement result. In one embodiment, the local host device uploads this data to backend server for historic usage. The noise in the PCG reveals heart murmur, and the relative position of each feature between the two waveforms are reflects the dynamics of heartbeat.

Figure 4:
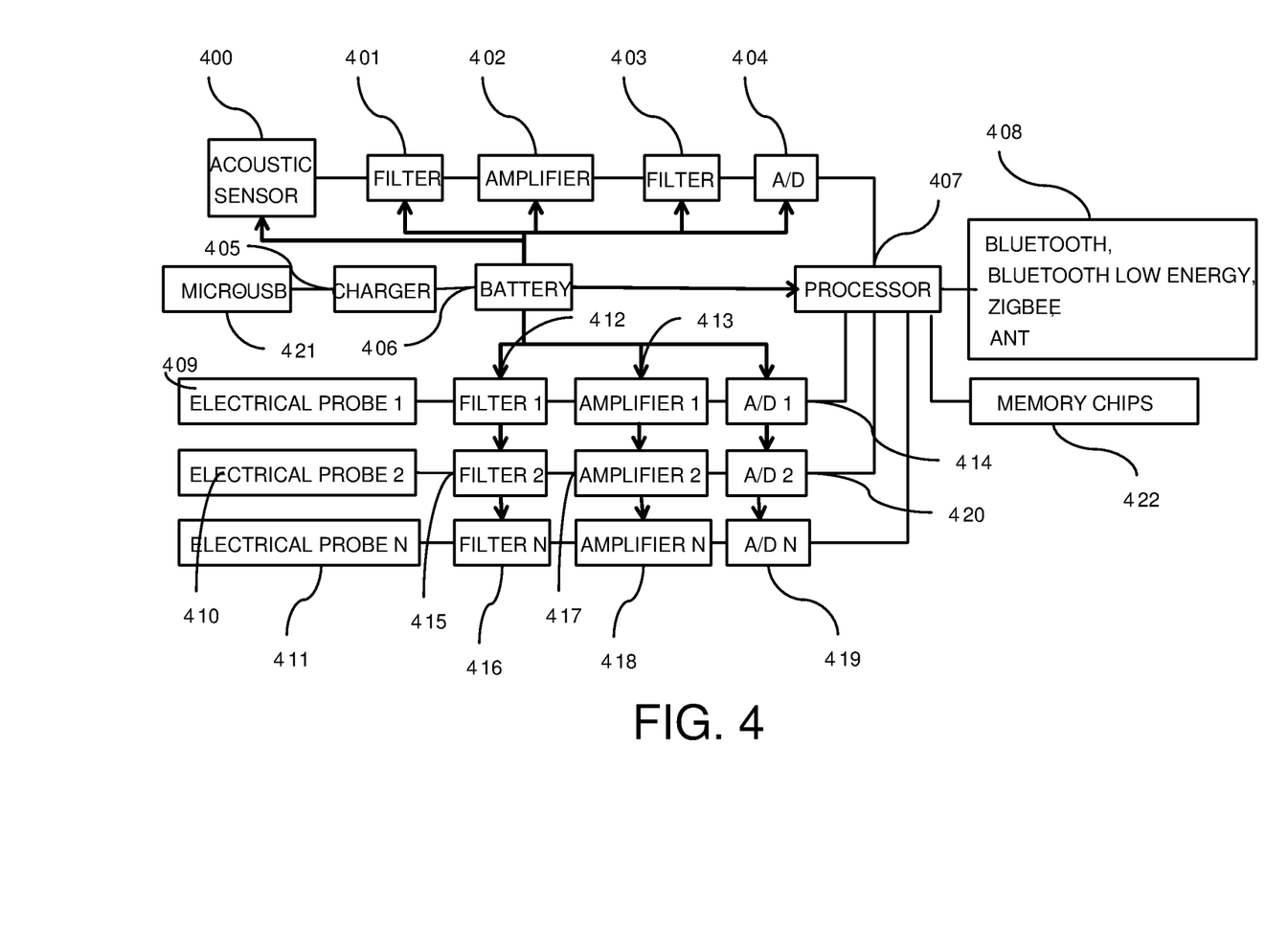
FIG. 4 shows electrical components inside the wearable device.

FIG. 4 shows the electronic circuit architecture. The circuit consists of five functional blocks: a battery power management, voltage detection circuit, heart sound detection circuit, processor, wireless communication circuit. The wearable power supply is a compact Li-polymer rechargeable battery (406) and it is charged by battery charge circuitry (405) which can be charged by any USB port through micro USB connector (421). The battery will supply power to all the functional blocks in FIG. 4. The power management circuit consists of power on/off tap switch, inrush current control circuit, over current, over voltage protection circuit. The microprocessor (407) is employed to monitor the voltage level of the battery (406), calculate the battery's energy status, and avoid system brown out. The acoustic-to-electric sensors (400) can be a simple microphone or a few microphones or piezo sensors to make up an array to have better noise immunity by better background measurement and better directive measurement. The sound from the body is measured by the sensor and the output of the sensor is electrical signal, which is connected to filter (401), amplifier (402), and filter (403) circuit, which is employed to cancel out environment noise, and enhance the body signal level. The microprocessor (407) is used to control this circuit to adjust the filter and amplifier to achieve the best signal-noise ratio. After noise cancellation and signal enhancement, the electric signal is connected to ADC (404) to convert the analog signal to digital data. The result is sent to microprocessor (407). To capture ECG, an array of low contact resistance voltage probe electrodes (409~411) are used, each probe electrode is followed by the filter (412, 415, 416) circuitry to condition the signal to the relevant frequency range to minimize the noise. In addition, the small signal is differentially amplified with reference to one of the electrodes in the electrode array to achieve a stable signal by amplifier circuit (413, 417, 418) array. This analog signal inputs to an ADC (414, 419, 420) and the output digital data are processed by the microprocessor (407). All the data can be saved in local memory chips (422), and transmitted to local host device through wireless communication circuit (408) which can be Bluetooth, or Bluetooth low energy, or ZigBee, or ANT protocol.

Figure 5:
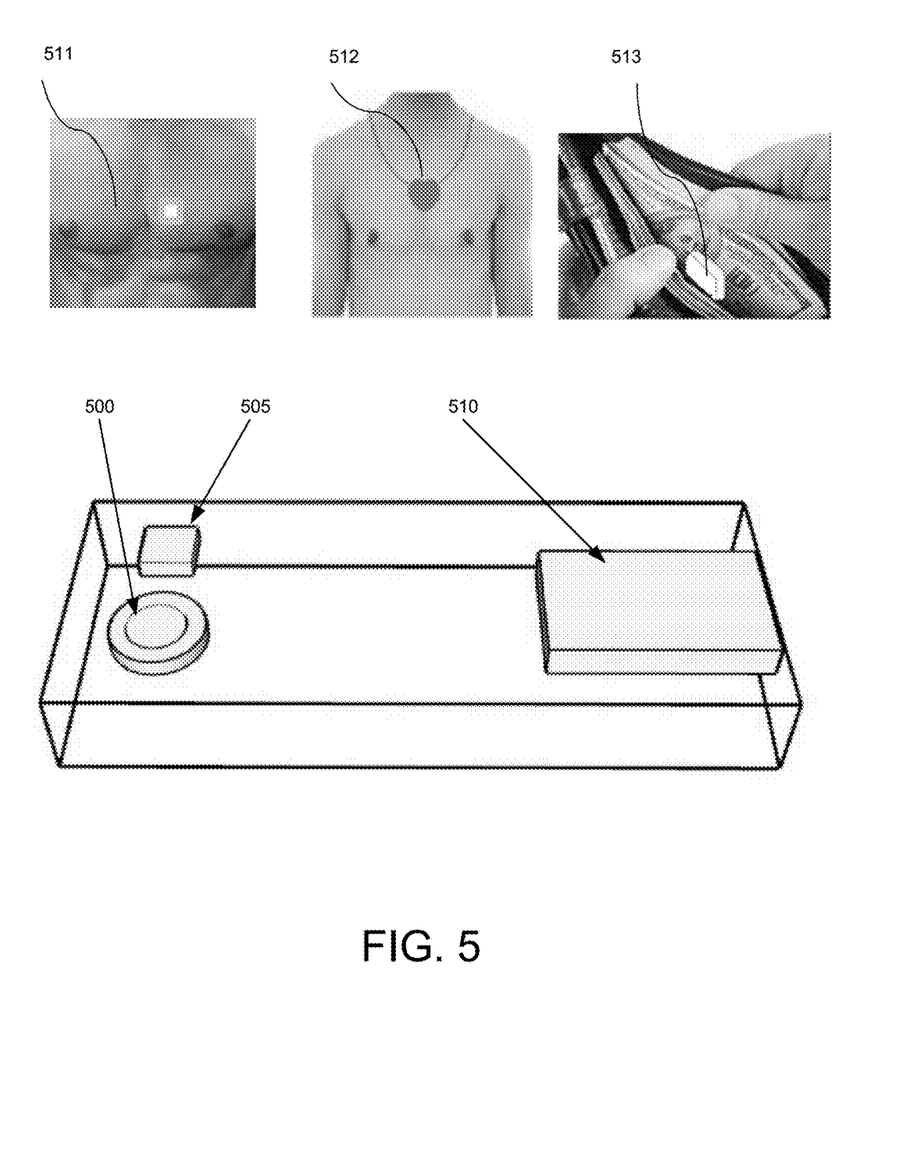
FIG. 5 illustrates several typical user scenarios.

FIG. 5 shows wearable examples. The wearable device is put on the chest by using a preformed patch (511). This wearable device can be carried by a necklace (512) or be carried in a wallet (513). The device can be embedded into a smartphone or similar device. It either can be part of the smartphone, or be pulled out to wear onto the body during usage and later be pulled into to recharge. The convenience is important factor to enable many applications. 500 is the smart phone camera, 505 is the flashlight of the smart phone. A waveform collecting and transmission module 510 is mounted at the bottom of the smart phone. The module is automatically charged using the smart phone battery when it is mounted on the smart phone.

Figure 6:
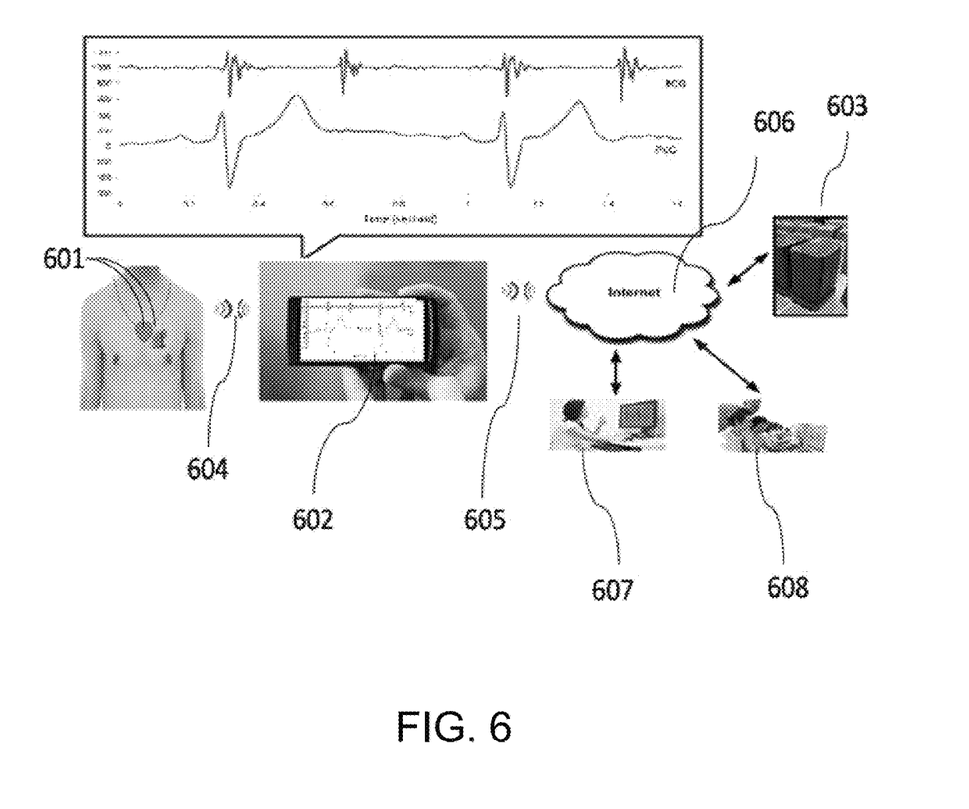
FIG. 6 illustrates the interaction between server, network, local host and the wearable device.

FIG. 6 illustrates the interaction of wearable device, local host device, and web server in data center. The figure is a typical implementation example with the wearable device in a patch on the chest (601), another alternative is to have it in a pouch of underwear and pressed against skin by the underwear's strip or tight fit mechanism. The wearable device communicates through short distance wireless communication protocol to local host device (602), a smart phone in this example; alternatives are tablet, PC, laptop, or local server. The local device connects to remote data center (603) through wireless (605) or wired (606) internet connections. The data sent to the data center can be automatically achieved and analyzed. The analysis includes comparing with user's historic data, comparing with various disease patterns and other more sophisticated analysis. With the permission of the user, the medical professionals (607) can access the user's data record to facilitate further medical examinations. With the permission of the user, the medical researchers, data mining experts (608) can utilize the data for large-scale data analysis and data mining. The wearable device (601) can also be integrated into or combined with other medical device or systems. For example, it can be used with glucose measuring device, blood pressure measuring device, body temperature measuring device, smart body weight measuring device, insulin pump, etc. In these application scenarios, the wearable device (601) offers an effective mean of heart monitoring, plus wireless data communication channel so that the continuous heart data plus other data collected from other medical devices can be transferred to the remote data center for achieve and analysis.

Figure 7:
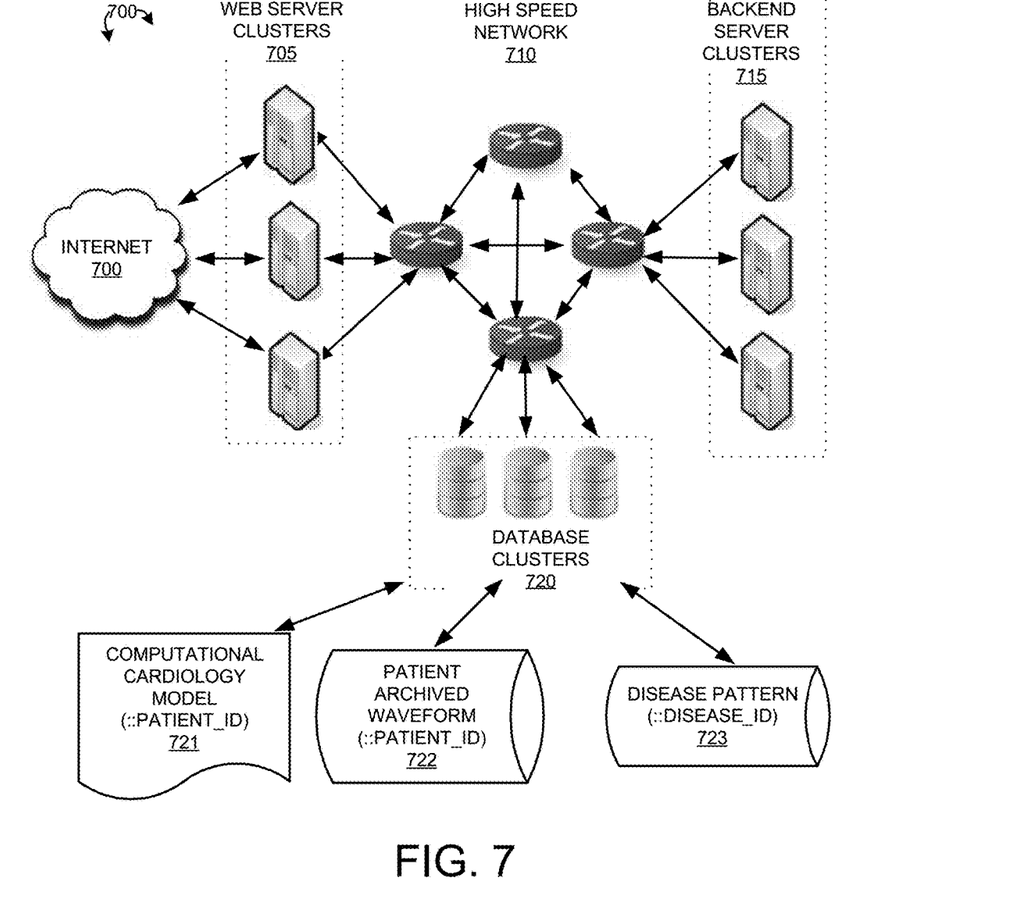
FIG. 7 is a diagram illustrates the architecture of data flow of the system from device to the local host, which can access the data processing and data storage in the data center.

FIG. 7 illustrates a network 700 with a remote data center in accordance with embodiments of the current invention. Network 700 consists of web server clusters 705, database clusters 720, and back end server clusters 715. These clusters are interconnected by a high-speed network 710. Smart device 105, computer 110 or local server 115 can connect to web server clusters 705 through an Internet 701 and transmit the waveforms data into the database clusters 720 of the remote data center. Back end server clusters 715 will get the waveforms from database clusters 720. Database clusters 720 stores achieved waveform information of patients, processes the information, and stores the process results including report into database clusters 720. Database clusters 720 may have multiple specific databases, such as computational cardiology mode database 721, patient archived waveform database 722, and disease pattern database 723. The user can use the smart device 105, computer 110 or local sever 115 to view the report, browse the analysis results, manage the account and archives, subscribe third party analysis algorithms. The web server clusters 705 take the roles as mediators to monitor the active user number, distribute the storage workload and computational workload, and make sure load balancing between servers. FIG. 7 only demonstrates one data center, as the user base growth, multiple data centers will be employed.

Figure 8:
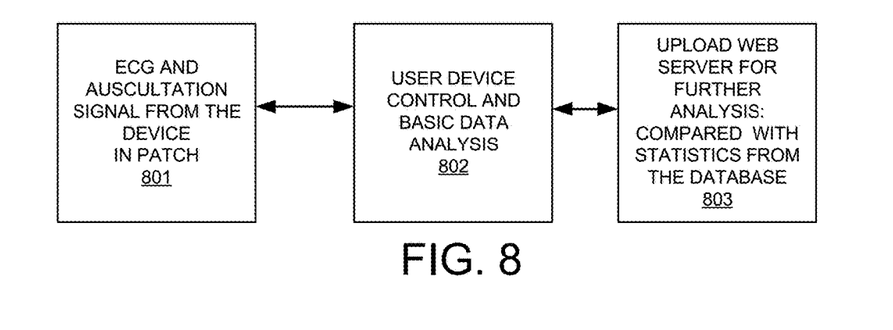
FIG. 8 is a block diagram illustrates the architecture of three levels of data processing.

As shown in FIG. 8, the digital data sent by the wearable device (801) is captured by the user's host device which has a device user interface (802) to set up and control the wearable device and also display the real time result from the wearable device, some device status and basic analysis results can also be displayed in real time, such as heart beat rate, systole duration, diastole duration, murmur free or not . . . , this report limited to the parameters can be derived through relative simple algorithm, by using wavelet transformation, auto correlation which is effective in determining valid data or invalid data and calculate basic timing information after the valid data is identified. On the other side, the user interface has the off device mode, which can replay and analyze any of previous saved data by using more advanced algorithm because the host device has more computing resource now without supporting the real time communication. In this phase, time domain, frequency domain analysis are used to calculate the rise time and fall time of the heart sounds S1 and S2, finding out the acoustic frequency of heart murmur. The user interface can also upload any of the saved data to the data center through encrypted data package for further statistical analysis (703), receive and view the analysis; post questions, algorithms requests and willing financial awards of the services to the remote data center or third party medical professionals, data analysis and data mining expertise. The user interface is also used to manage the account and archives, subscribe third party analysis algorithms. The remote data center receives the waveform and store them into the database. It is very likely that certain parts of received waveform contain overwhelming environmental background noise. In another scenario, certain parts of the received waveform may contain very weak signal or invalid signal. The algorithm mentioned above is used to identify the valid portion and skip these invalid sections. For the valid sections of the received waveform, noise filter is employed to filter out body noise and environmental noise. The abnormal sections of the waveform are compared against various disease patterns to find matches or identify similarities. The analysis results will be stored into database. Computational cardiology model of the user can be used to predict the waveform. The valid sections of received waveform will compare against predicted waveform. If there are mismatches, the back end server will adjust the parameters to try to match the received waveform. The matching details, adjustments, conclusions, failure reports will be stored into database. The user can pre-select third party analysis algorithms. According to user's selections, the back end server will apply the third party algorithms to the valid sections of the received waveform. The analysis results and reports will be stored into the database. If the third party's analysis algorithms are not free, the user will be charged for the service, and the charge detail will be recorded into the database. This report will be stored into the database. When the report is ready, user will be informed through web server by email, SMS, or other methods. The user can also login the web server (803) to view the report and analysis details.

Figure 9:
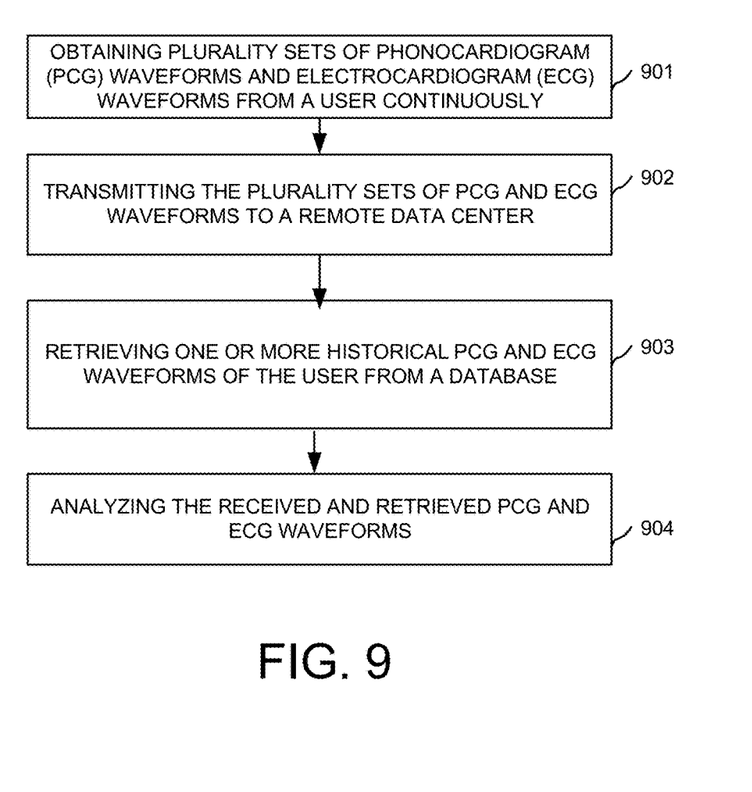
FIG. 9 is a flow chart obtaining and analyzing received PCG and ECG waveforms based on retrieved historical waveforms in accordance with embodiments of the current invention.

FIG. 9 is a flow chart obtaining and analyzing received PCG and ECG waveforms based on retrieved historical waveforms in accordance with embodiments of the current invention. Step (901) obtains plurality sets of phonocardiogram (PCG) waveforms and electrocardiogram (ECG) waveforms from a user continuously. Step (902) transmits the plurality sets of PCG and ECG waveforms to a remote data center. Step (903) retrieves one or more historical PCG and ECG waveforms of the user from a database. Step (904) analyzes the received and retrieved PCG and ECG waveforms.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. An apparatus comprising:
a wearable size container, wherein the container has an inner chamber and an outer surface, wherein the container can be attached to a body;
one or more micro acoustic-to-electric sensors mounted on the inner chamber of the container, wherein the one or more micro acoustic-to-electric sensors detect acoustic signal from the attached body and convert the acoustic signal to electrical signal corresponding to phonocardiogram (PCG) waveform;
an array of voltage electrodes that measure electrocardiogram (ECG) waveform mounted on the inner chamber of the container;
a layer of a noise seal attached to the container, wherein the noise seal shields environmental noises and friction noises from body movements;
one or more convertors connecting to the one or more micro acoustic-to-electric sensors and the array of voltage electrodes, wherein one or more convertors digitizes sensor waveform outputs;
a non-volatile storage that stores the digitized waveforms; and
a micro-processor that collects and analyzes PCG and ECG waveforms and adjusts one or more settings for the apparatus, wherein the micro-processor further connects one or more user input units, and wherein the micro-processor adjusts one or more settings for the apparatus based on one or more user inputs, and where in the one or more settings for the apparatus are adjusted based on one or more body conditions comprising: skin conditions, movement conditions, ages, and personal data.

2. The apparatus of claim 1, further comprising: a flexible patch with medical grade adhesive attaching to the outer surface of the container such that the container can be mounted to a fixed body position.

3. The apparatus of claim 2, wherein the flexible patch is part of the noise seal.

4. The apparatus of claim 1, wherein the noise seal layer is a ring-shaped layer attached to container, and wherein the ring-shaped layer surrounds the one or more micro acoustic-to-electric sensors and the array of voltage electrodes.

5. The apparatus of claim 1, further comprising: a wireless communication circuitry, wherein the wireless communication circuitry communicates with one or more smart devices through a wireless network.

6. The apparatus of claim 1, further comprising: a noise cancellation and gain control circuit associated with the one or more acoustic-to-electric sensors to reduce environmental noises and enhance PCG waveforms.

7. The apparatus of claim 1, wherein the settings comprising: an adjustable gain for the acoustic-to-electrical sensors, and an adjustable gain for the voltage electrodes.

* * * * *